United States Patent [19]
Gyory et al.

[11] Patent Number: 5,985,316
[45] Date of Patent: Nov. 16, 1999

[54] COMPOSITION AND METHOD OF ENHANCING ELECTROTRANSPORT AGENT DELIVERY

[75] Inventors: J. Richard Gyory, San Jose; Patricia S. Campbell, Palo Alto, both of Calif.

[73] Assignee: Alza Corporation, Palo Alto, Calif.

[21] Appl. No.: 08/431,188

[22] Filed: Apr. 28, 1995

[51] Int. Cl.⁶ .............................. A61N 1/30; A61M 37/00
[52] U.S. Cl. ............................................ 424/449; 514/947
[58] Field of Search .......................... 424/444; 514/946, 514/947, 558; 604/20

[56] References Cited

U.S. PATENT DOCUMENTS

| | | | |
|---|---|---|---|
| 4,605,670 | 8/1986 | Saito et al. | 514/619 |
| 4,637,930 | 1/1987 | Konno et al. | 424/13 |
| 4,722,726 | 2/1988 | Sanderson et al. | 604/20 |
| 4,731,241 | 3/1988 | Yamada et al. | 514/227 |
| 4,820,263 | 4/1989 | Spevak et al. | 604/20 |
| 4,882,163 | 11/1989 | Guse et al. | 424/448 |
| 4,892,737 | 1/1990 | Bodor et al. | 424/449 |
| 5,001,139 | 3/1991 | Lawter et al. | 514/344 |
| 5,023,085 | 6/1991 | Francoeur et al. | 424/449 |
| 5,045,553 | 9/1991 | Ueda et al. | 514/344 |
| 5,069,909 | 12/1991 | Sharma et al. | 424/449 |
| 5,128,376 | 7/1992 | Saito et al. | 514/772 |
| 5,422,118 | 6/1995 | Brown et al. | |
| 5,432,192 | 7/1995 | Sawanishi et al. | |
| 5,668,170 | 9/1997 | Gyory . | |

FOREIGN PATENT DOCUMENTS

| | | | |
|---|---|---|---|
| 0435436A2 | 7/1991 | European Pat. Off. | A61K 47/22 |
| 0552879 | 7/1993 | European Pat. Off. | A61K 47/10 |
| 1574340 | 9/1980 | United Kingdom | A61K 31/52 |
| 2239803 | 7/1991 | United Kingdom | A61N 1/30 |
| WO8900853 | 2/1989 | WIPO | A61K 31/60 |
| WO9008507 | 8/1990 | WIPO | A61B 10/00 |
| WO9116077 | 10/1991 | WIPO | A61K 47/12 |
| WO9301807 | 2/1993 | WIPO | A61K 9/70 |
| WO9410987 | 5/1994 | WIPO | A61K 9/70 |

OTHER PUBLICATIONS

Srinivasan et al., J. Pharm. Sci. 79(7):588–91 (1990).

*Primary Examiner*—Edward J. Webman
*Attorney, Agent, or Firm*—Steven F. Stone; D. Byron Miller; Owen J. Bates

[57] ABSTRACT

An electrotransport device (10) for transdermal delivery of an agent through a body surface has a donor reservoir (16) which contains a compound formed of the agent and a transdermal permeation enhancer, the compound being able to dissociate into an agent ion and an enhancer counter ion. Methods of enhancing transdermal electrotransport drug delivery and methods of forming a composition exhibiting enhanced transdermal electrotransport drug delivery are also provided.

25 Claims, 1 Drawing Sheet

5,985,316

COMPOSITION AND METHOD OF ENHANCING ELECTROTRANSPORT AGENT DELIVERY

TECHNICAL FIELD

This invention relates to the delivery of agents through a body surface by electrotransport. More particularly, the invention relates to the enhancement of electrotransport agent delivery with the aid of permeation enhancers while avoiding the effects of competing ions.

BACKGROUND ART

The transdermal delivery of drugs, by diffusion through the epidermis, offers improvements over more traditional delivery methods, such as subcutaneous injections and oral delivery. Transdermal drug delivery avoids the hepatic first pass effect encountered with oral drug delivery. Transdermal drug delivery also reduces patient discomfort when compared to subcutaneous injection. In addition, transdermal drug delivery can provide more uniform concentrations of drug in the bloodstream of the patient over time due to the extended controlled delivery profiles of certain patches. The term "transdermal" delivery, broadly encompasses the delivery of an agent through a body surface, such as the skin, mucosa, or nails of an animal.

The skin functions as the primary barrier to the transdermal penetration of materials into the body and represents the body's major resistance to the transdermal delivery of therapeutic agents such as drugs. To date, efforts have been focussed on reducing the physical resistance, or enhancing the permeability, of the skin to the delivery of the therapeutic agent by passive diffusion. Various methods for increasing the rate of transdermal drug diffusion have been used. For example, drug-impermeable backing layers made of metal, plastic and other materials have been employed in skin patches in order to limit diffusion of drugs away from the skin, increase the hydration of the skin and, thereby, increase the rate of diffusion of drugs through the skin. Increases in the rate of absorption of agents through the skin have been produced by varying the temperature and the relative humidity of the atmosphere adjacent to the skin. Other efforts have been directed at abrading or piercing the skin by mechanically disrupting its outermost stratum corneum layer. Chemical absorption promoters ( also referred to as flux enhancers or permeation enhancers) have also been utilized, both as integral components of transdermal therapeutic drug delivery devices or as a composition applied to the skin as a pretreatment step before applying the transdermal patch.

The utility of fatty acid permeation enhancers in passive transdermal drug delivery has been previously recognized (see, for example, U.S. Pat. Nos. 5,045,553 and 5,023,085 (fatty acid with additional cycloketone)). Similarly, U.S. Pat. Nos. 5,069,909 (for buprenorphine), 5,001,139 and 4,892,737 disclose the use of fatty acid esters in mixtures with other enhancers for passive transdermal delivery. More generally, $C_5$–$C_{30}$ aliphatic monocarboxylic acids are disclosed as transdermal drug permeation enhancers in U.S. Pat. No. 4,731,241 for the passive delivery of N-ethoxycarbonyl-3-morpholino sydnonimine. U.S. Pat. No. 4,892,737 utilizes a mixture of quaternary ammonium salts with saturated and unsaturated aliphatic carboxylic acids for the passive transdermal electrotransport of agents. U.S. Pat. No. 4,882,163 passively delivers monoxidine with the aid of an alkyl aliphatic acid of at least 12 C-atoms. In U.S. Pat. No. 4,637,930, $C_6$–$C_{12}$ fatty acid esters are used for the delivery of nicardipine hydrochloride.

A composition for the passive delivery of salicylic acid, which comprises aliphatic diols, an ester of a mono- or polyhydric alcohol and a saturated fatty acid is disclosed in published PCT patent application WO 90108507. A composition containing salicylic acid, an aliphatic 1,2-diol such as propane- or butane-diol, and a fatty oil, such as triglycerides and their fatty acid derivatives, is disclosed in published PCT patent application WO 89/00853. U.S. Pat. Nos. 4,605,670 and 5,128,376, in addition, disclose the passive percutaneous administration of an active agent in a composition containing a mixture of (1) an ester of a $C_7$–$C_{18}$ aliphatic acid and an alcohol, a $C_8$–$C_{26}$ aliphatic monoalcohol, or mixtures thereof, and (2) $C_4$–$C_6$ cyclic amides such as pyrrolidones, and diols, triols, or mixtures thereof.

Generally, these passive methods have had only limited success in significantly increasing the transdermal flux of drug. Transdermal drug permeation rates (fluxes) can be increased over that obtained with passive diffusion by using electrically assisted transport, ie, electrotransport. The term "electrotransport" as used herein refers to delivery of an agent through a body surface (eg, skin) with the assistance of an electrical field. Electrotransport, thus, refers generally to the passage of an agent through a body surface, such as the skin, mucous membranes, or nails, which is at least partially induced by applying an electrical current through the surface. Many therapeutic agents, including drugs, may be introduced into the human body by electrotransport. The electrotransport of an agent through a body surface may be attained by one or more of several known phenomena. One widely used electrotransport phenomenon is iontophoresis, which involves the electrically induced transport of charged ions. Electroosmosis, another type of electrotransport, involves the movement of a liquid, which liquid contains one or more therapeutic agent(s) dissolved therein, through a biological membrane under the influence of an electrical field. Electroporation, still another type of electrotransport, involves the movement of an agent through transiently-created pores formed in a biological membrane under the influence of an electric field. When any given agent is electrotransported, more than one of these phenomena, including passive diffusion, may occur simultaneously to some extent. The term electrotransport, as used herein, is given its broadest possible interpretation to include the electrically induced or enhanced transport of charged species, uncharged species, or mixtures thereof, regardless of the specific mechanism(s) by which the agent(s) is(are) actually transported.

Electrotransport devices require at least two electrodes, both being in electrical contact with some portion of the skin, nails, mucous membrane, or other membrane surfaces of the body. One electrode, commonly referred to as the "donor" or "active" electrode, is the electrode from which the therapeutic agent, such as a drug or prodrug, is delivered into the body. The other electrode, typically termed the "counter" or "return" electrode, serves to close the electrical circuit through the body. For example, if a cationic (ie, a positively charged) agent is to be delivered, the anode will be the active or donor electrode while the cathode is the counter electrode. Alternatively, if the agent to be delivered is an anion (ie, a negatively charged ion) the cathode will be the donor electrode while the anode is the counter electrode. When anionic and cationic drugs need to be delivered at the same time, both the anode and cathode may be used for this purpose and the anionic drug placed in the cathode while the cationic drug is placed in the anode. In addition, electrotransport delivery devices include an electrical power source, typically in the form of one or more batteries, and optionally electrical control circuitry which regulates the flow of electric current through the electrodes and thereby the rate of drug delivery. Alternatively, the power may be supplied, at least in part, by a galvanic couple formed by contacting two electrodes made of dissimilar materials. A complete electrical circuit is formed by electrically contacting one pole of the power source to the donor electrode, the donor electrode to the body, the body to the counter electrode, and the counter electrode to the opposite pole of the power source.

The donor electrode typically includes a reservoir containing a solution of the therapeutic agent or drug to be delivered. The donor reservoir may take the form of a pouch, a cavity, a porous sponge, a pad, and a pre-formed gel body, among others. The counter electrode likewise typically includes a reservoir containing a biocompatible electrolyte salt solution. Such reservoirs are electrically connected to the anode or cathode of the electrotransport device to provide either a fixed or a renewable source of one or more therapeutic agents or drugs.

It is known that electrotransport drug flux is roughly proportional to the level of electric current applied by the device. However, there is a limit to the current density (current density is the level of electric current (mA) applied by the device divided by the skin contact area ($cm^2$) of the electrodes) which may be comfortably tolerated by a patient. This limit on the level of current density which may be comfortably tolerated by a patient becomes more problematic as the size of the electrotransport system and, therefore, the skin contact areas of the electrodes, is reduced, ie, for electrotransport systems which are designed to be wearable. Thus, there is a limit to the level of electric current which may be applied by any electrotransport device of a given size and this current limit becomes lower as the size or the skin contact area of the device is reduced. In certain instances, electrotransport devices operating at these current limits have been unable to deliver therapeutically effective amounts of drugs. In those cases, the incorporation of a permeation enhancer into the electrotransport device may increase the amount of the agent delivered to adequate (ie, therapeutic) levels.

In the context of this application, the terms "flux enhancer" and permeation enhancers broadly describe a chemical species which either reduces the physical resistance of a body surface to the passage of an agent therethrough, alters the ionic selectivity of the body surface, increases the electrical conductivity or the permeability of the body surface, and/or the number of pathways therethrough. The use of electrotransport permeation enhancers to reduce skin resistance also helps reduce the size of the electrotransport device by requiring a reduced electrical potential (ie, voltage) to generate a particular level of electric current (ie, mA) through the skin and thereby reduce the size and/or number of batteries needed to power the device. The use of electrotransport permeation enhancers can increase the amount of drug which is electrotransported per unit of applied electric current. Therefore, electrotransport permeation enhancers can reduce the amount of current, and hence also reduce the current density applied by a device of a given size and/or reduce the size (ie, skin contact area) of the donor and counter electrodes, needed to achieve a target transdermal drug flux. A reduction in the size of, and/or current applied by, the device also improves patient comfort and a reduction in the number of batteries reduces the cost of the device.

A limited number of permeation enhancers for the electrotransport delivery of therapeutic agents have been disclosed in the literature. Ethanol has been utilized as a permeation enhancer for electrotransport delivery of polypeptides. See Srinivasan et al, J. Pharm. Sci. 79(7):588–91 (1990). In U.S. Pat. No. 4,722,726 to Sanderson et al., the skin is pretreated with an ionic surfactant (eg, sodium lauryl sulfate) to reduce competition with tissue ions migrating outwardly through the skin. Francoeur et al, U.S. Pat. No. 5,023,085 discloses the use of unsaturated $C_{14}$–$C_{20}$ acids, alcohols, amines, and esters, along with ketones for the iontophoretic delivery of certain drugs. Published PCT patent application WO91/16077 discloses the use of fatty acids, such as oleic acid, lauric acid, capric acid, and caprylic acid, as permeation enhancers for the iontophoretic delivery of drugs. European Patent Application 93/300198.4 discloses delivering therapeutic agents transdermally by iontophoresis with the aid of a broadly described group of "lipid modifiers". The modifiers are generally described as having a $C_5$–$C_{28}$ aliphatic chain and moieties such as hemiacetals amids, acetals, alcohols, carboxylic acids, esters, and others, but containing no more than 50 to 60 carbon atoms. Only a few dioxolanes, an aliphatic carbonate, and a pyrrolidone are exemplified.

A problem which arises with the addition of a permeation enhancer to the donor reservoir composition of an electrotransport device is that extraneous ions which compete with the therapeutic agent ions for transport through the body surface are introduced into the composition. For example, the addition of sodium laurate to a cationic drug-containing donor reservoir composition will have two opposing effects. The laurate ions will increase skin permeability, and hence increase the electrotransport drug delivery rate. On the other hand, the sodium ions will compete with the cationic drug for transport through the body surface and, thus, reduce the rate of electrotransport drug delivery. The sodium ions, in this context, are termed "competing ions". As used herein, this term refers to ionic species having the same (ie, same sign) charge as the therapeutic agent to be delivered by electrotransport, and which may be delivered through the body surface in its place.

DISCLOSURE OF THE INVENTION

The present invention provides a method of adding a permeation enhancer to the donor reservoir of an electrotransport delivery device which substantially avoids the introduction of competing ions thereto. An electrotransport donor reservoir composition, including both a therapeutic agent and a permeation enhancer but substantially free of competing permeation enhancer ions, is also provided. The invention involves a composition comprising the therapeutic agent to be delivered, wherein the agent is in the form of an agent-enhancer compound. The agent-enhancer compound may be formed by reacting the agent, in the form of a base, with an acid permeation enhancer, such as a fatty acid. Alternatively, the agent-enhancer compound may be formed by reacting the agent in the form of an acid, with a base permeation enhancer, such as a pyrrolidone. The agent-enhancer compound is preferably a water soluble salt. When the agent enhancer compound is dissolved in a liquid (eg, aqueous) solvent, a solution comprised of therapeutic agent ions and oppositely charged permeation enhancer counterions is formed. The solution is substantially free of competing permeation enhancer ions having the same charge as the therapeutic agent ions. The invention also contemplates an electrotransport delivery device comprising donor and counter electrodes wherein the donor electrode contains the composition of this invention.

The invention will now be described in further detail with reference to the accompanying drawings.

MODES FOR CARRYING OUT THE INVENTION

Figure 1:
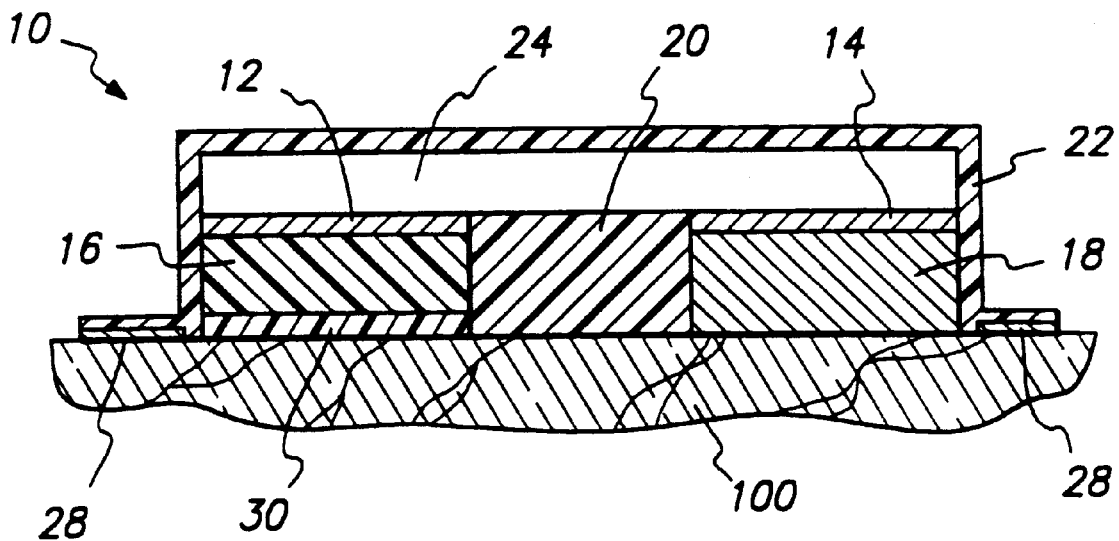
FIG. 1 is a sectional view of an electrotransport agent delivery device which represents one embodiment of the present invention.

The present invention utilizes a therapeutic agent-enhancer compound to avoid the introduction of competing ions (ie, ions having the same sign charge as the therapeutic agent ions) into the donor reservoir composition of an electrotransport delivery device.

In general, permeation enhancers cause higher electrotransport agent flux at a given level of applied electric current compared to the flux of the agent, at the same applied current level, but in the absence of the flux enhancer. In accordance with this invention, the agent to be delivered by electrotransport is formulated as an agent-enhancer compound, and more preferably as an agent-enhancer salt. The agent-enhancer compound can be formed by one of the following two reactions; (1) reacting a base therapeutic agent with an acid permeation enhancer to form an agent-enhancer compound, preferably in the form of a water soluble salt, which compound when dissolved in a liquid solvent forms agent cations and permeation enhancer anions; and (2) reacting an acid therapeutic agent with a base permeation enhancer, to form an agent-enhancer compound, preferably in the form of a water soluble salt, which compound when dissolved in a liquid solvent forms agent anions and permeation enhancer cations. The former agent-enhancer compound is suitable for delivery from an anodic electrode of an electrotransport delivery device while the latter agent-enhancer compound is suitable for delivery from a cathodic electrode of an electrotransport delivery device.

The above two reactions substantially avoid adding competing ions to the donor reservoir composition since the byproduct of the acid base reaction is neutral water. Examples of suitable acid-base reactions according to the present invention are shown below.

Examples of reactions between various forms of a base therapeutic agent (D) and an acid permeation enhancer (H-Enh) include:

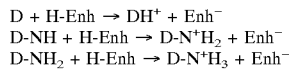

Examples of reactions between an acid therapeutic agent (H-D) and various forms of a base permeation enhancer (N-Enh):

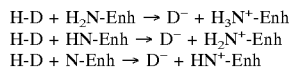

When an agent-enhancer compound is utilized in the present composition, the choice of the permeation enhancer for the electrotransport delivery of the present invention turns on the charge of the therapeutic agent ions to be delivered. For example, if the therapeutic agent is a base and the ionized form of the therapeutic agent delivered by electrotransport is cationic (eg, a protonated base), the permeation enhancer is preferably an acid. The reaction of the base agent with the acid enhancer forms an ionizable salt which when dissolved in a liquid solvent forms positively charged agent ions and negatively charged permeation enhancer counter ions. For example, the local anesthetic lidocaine [$(CH_3)_2$—$C_6H_3$—$NHCOCH_2N(C_2H_5)_2$] is a base (ie, a tertiary amine) which forms a salt, i.e. lidocaine hydrolaurate, upon reaction with the acid permeation enhancer lauric acid. In aqueous solution, lidocaine hydrolaurate forms protonated lidocaine cations and laurate anions.

Examples of base therapeutic agents which can be reacted with an acid permeation enhancer to form an agent-enhancer compound which can be delivered by electrotransport (ie, in a predominantly cationic form) include lidocaine, fentanyl, metoclopramide, ondansetron, verapamil and terbutaline, among others.

Preferred acid permeation enhancers are organic acids, and preferred organic acids are $C_8$–$C_{18}$ alkyl, alkenyl and alkenyl fatty acids, and still more preferred are $C_{10}$–$C_{14}$ acids. Most preferred are $C_{10}$–$C_{12}$ acids. The organic acids useful as electrotransport permeation enhancers in this invention have the general chemical formula R—COOH, where R may be a straight or branched, linear or cyclic alkyl, alkenyl, or alkynyl group, including without limitation, carbon chains having 8 to 18 carbon atoms, and preferably $C_{10}$–$C_{14}$ acids. In this class of acid permeation enhancers can be mentioned acids such as lauric acid (dodecanoic acid), oleic acid (9,10-octadecanoic acid), capric acid (decanoic acid), and caprylic acid (octanoic acid), among others.

Alternatively, if the therapeutic agent is an acid and the ionized form of the therapeutic agent delivered by electrotransport is anionic (eg, D—COO—), the permeation enhancer is preferably a base. The reaction of the acid agent with the base enhancer forms an ionizable salt which when dissolved in a liquid solvent forms negatively charged agent ions and positively charged permeation enhancer counter ions. For example, the non-steroidal anti-inflammatory drug (NSAID) ketoprofen is an acid (ie, a carboxylic acid) which forms a salt, ie, methyl pyrrolidone hydro-m-benzoyl hydratropate, upon reaction with methyl pyrrolidone. In aqueous solution, methyl pyrrolidone hydro-m-benzoyl hydratropate forms protonated methyl pyrrolidone cations and ketoprofen anions.

Examples of acid therapeutic agents which are delivered by electrotransport in a predominantly anionic form include anti-inflammatory agents such as aspirin, tolmetin, fenoprofen, ibuprofen, ketoprofen, indomethacin, and ketorolac, salicylic acid and its derivatives such as diflunisal and diclofenac, salicylic acid and its derivatives such as diflunisal and diclofenac, cromolyn, naproxen, zomepirac, prostaglandins, valproic acid and captopril, among others.

Preferred base permeation enhancers are pyrrolidones such as methyl pyrrolidone and dodecylpyrrolidone, piperidine and laurocapram.

The concentration of the therapeutic agent in the donor reservoir composition depends on various factors, including its potency, the magnitude and the duration of the applied current, the concentration of the enhancer, and the pH of the composition. Generally, the concentration of the therapeutic agent in the composition ranges from about 10 to 100,000 μg/ml, and more preferably, from about 100 to about 50,000

μg/ml. Similarly, the preferred ratio of the different forms of the agent in the composition is also a function of the specific delivery conditions. Generally, from 1 to 100 wt % of the total agent concentration is present in the charged (ie, ionic) form, and more preferably, about 10 to 100 wt %. Furthermore, the therapeutic agent may be present in the donor reservoir in only agent-enhancer salt/solution form or as a mixture with other therapeutic agent salts (eg, in the case of lidocaine, the lidocaine present in the donor reservoir may comprise 100% lidocaine hydrolaurate or a mixture of lidocaine hydrolaurate and lidocaine hydrochloride). The relative amount of agent-enhancer compound present in the donor reservoir will vary depending upon the concentration of flux enhancer needed to achieve a flux enhancing effect and also upon the mode of operation of the electrotransport delivery device. For example, if the device is initially run in a "reverse polarity" mode to deliver actively (ie, by electromigration) the enhancer ions, a lower concentration of enhancer ions may be needed compared to a mode of operation wherein the polarity of the donor electrode is fixed to deliver the therapeutic agent ions by electromigration. Typically, the weight fraction of therapeutic agent in the donor reservoir which is in the form of the agent-enhancer compound is at least about 5 wt % and preferably at least about 10 wt % of the total therapeutic agent present in the reservoir.

The preferred pH of the donor reservoir is also a function of numerous factors, including the charge of the therapeutic agent ions being delivered, i.e. whether the agent is cationic, anionic, or amphoteric, the desired delivery rate, and the degree of irritation and sensitization which is produced by the particular therapeutic agent being delivered and the particular delivery regimen (e.g., applied current level, duration, etc). Cationic therapeutic agents are preferably delivered from an anodic donor reservoir having a pH of about 6 to 9, and more preferably about 7.5 to 8.5 whereas anionic therapeutic agents are preferably delivered from a cathodic reservoir having a pH of about 3 to 6, and more preferably about 3.5 to 5. These pH ranges are subject to exceptions for those drugs which exhibit poor solubility in these particular anodic/cathodic pH ranges.

This invention is useful for the delivery of a broad class of agents that are deliverable through body surfaces and membranes, including the skin, mucosa and nails. As used herein, the terms "agent" and "therapeutic agent" are used interchangeably and are intended to mean in the broadest sense any pharmaceutically-acceptable agent, and preferably therapeutically active substances, such as drugs or prodrugs, which are delivered to a living organism to produce a desired, and usually beneficial, effect. In general, this includes therapeutic agents in all of the major therapeutic areas including, but not limited to, anti-infectives such as antibiotics and antiviral agents; analgesics such as fentanyl, sufentanil, and buprenorphine, and analgesic combinations; anesthetics; anorexics; antiarthritics; antiasthmatic agents such as terbutaline; anticonvulsants; antidepressants; antidiabetics agents; antidiarrheals; antihistamines; antiinflammatory agents; antimigraine preparations; antimotion sickness preparations such as scopolamine and ondansetron; antinauseants; antineoplastics; antiparkinsonism drugs; antipruritics; antipsychotics; antipyretics; antispasmodics including gastrointestinal and urinary; anticholinergics; sympathomimetrics; xanthine derivatives; cardiovascular preparations including calcium channel blockers such as nifedipine; beta-agonists such as dobutamine and ritodrine; beta blockers; antiarrythmics; antihypertensives such as atenolol; ACE inhibitors such as ranitidine; diuretics; vasodilators including general, coronary, peripheral and cerebral; central nervous system stimulants; cough and cold preparations; decongestants; diagnostics; hormones such as parathyroid hormones; hypnotics; immunosuppressives; muscle relaxants; parasympatholytics; parasympathomimetrics; prostaglandins; proteins; peptides; psychostimulants; sedatives and tranquilizers.

More specifically, this invention is useful in the electrotransport delivery of agents which may be produced in either an acid or base forms. An "acid form", as used herein, refers to a form of the agent which is a Lewis acid, i.e. any form of the agent which can attach itself to a chemical moiety with an unshared pair of electrons. Similarly, a "base form", as used herein, refers to a form of the agent which possesses an unshared pair of electrons.

The invention, therefore, may be applied to a wide variety of agents which have a base or an acid form. A preferred category of "base" drugs is amines. Typically, amines have an $R_nN$ moiety which reacts with an acid to form an $R_nN—H^+$ protonated ion form in which the hydrogen atom is associated with, or weakly bonded to, the nitrogen atom. The protonated form is the form of the therapeutic agent which is typically delivered from an anodic electrode during electrotransport delivery. Examples of amine drugs which can be reacted with an acid permeation enhancer to form a protonated drug ion include, without limitation, buspirone, diltiazem, encainide, fentanyl, lidocaine, metoclopramide, midazolam, nicardipine, prazosin, scopolamine, tetracaine, and verapamil, among others. A particularly useful amine drug for electrotransport delivery in accordance with this invention is lidocaine base which can be reacted with an acid permeation enhancer, such as lauric acid, to form an agent-enhancer compound (eg, lidocaine hydrolaurate).

A preferred category of "acid" drugs is carboxylic acid drugs, having a D—COOH structure. The hydrogen atom of the carboxyl group is donated to the base enhancer to form a therapeutic agent anion (eg, D—COO—) and a protonated base enhancer counter cation (eg, $H_nN^+$—Enh). Examples of preferred carboxylic acid drugs include ketoprofen, ibuprofen, fenoprofen, tolmetin, ketorolac, diflunisal, naproxen, zomepirac, valproic acid, aspirin, prostaglandin E1, diclofenac, captopril, and cromolyn. Examples of acid drugs which are not carboxylic acids include piroxicam and dexamethasone phosphate.

The invention has utility in the electrotransport delivery of peptides, polypeptides, proteins, and other macromolecules which are otherwise difficult to deliver transdermally or transmucosally because of their size. These macromolecular substances typically have a molecular weight of at least about 300 Daltons, and more typically, a molecular weight in the range of about 300 to 40,000 Daltons. However, smaller and larger peptides are also deliverable in accordance with this invention. Examples of peptides and proteins which may be delivered in accordance with the present invention include, without limitation, LHRH, LHRH analogs such as buserelin, gonadorelin, naphrelin and leuprolide, GHRH, GHRF, insulin, insulinotropin, heparin, calcitonin, octreotide, endorphin, TRH, NT-36 (chemical name: N-[[(s)-4-oxo-2-azetidinyl]carbonyl]-L-histidyl-L-prolinamide], liprecin, pituitary hormones, e.g. HGH, HMG, HCG, desmopressin acetate, follicle luteoids, α-ANF, growth factor releasing factor (GFRF), β-MSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hirulog, hirudin analogs, hyaluronidase, interferon, interleukin-2, menotropins, e.g. urofollitropin (FSH) and LH, oxytocin, streptokinase, tissue plasminogen activator, urokinase, vasopressin, desmopressin, ACTH analogs, ANP, ANP clearance inhibitors, angiotensin 11 antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 antitrypsin (recombinant), and TGF-beta, as an agent-enhancer compound.

Referring now to FIG. 1, one example of a unitary electrotransport device 10 useful in accordance with the present invention is illustrated. The device 10 has two current distributing members or electrodes, made of electrically conductive materials, referred to herein as donor electrode 12 and counter electrode 14. The electrodes may be composed of any materials which are sufficiently electrically conductive including, without limitation thereto, silver, silver chloride, carbon, zinc, and stainless steel. The electrodes may have various forms including metal foil, screen, coatings and polymer matrices loaded with electrically conductive fillers such as powdered metal, e.g. silver or carbon. Such matrices may be formed by conventional processes such as extrusion, calendering, film evaporation, or spray coating. In FIG. 1, the donor and counter electrodes 12 and 14 are positioned adjacent to, and in electrical contact with, the donor reservoir 16 and the counter reservoir 18, respectively. The donor reservoir 16 contains a solution of the agent to be delivered, while the optional counter reservoir 18 contains a solution of a biocompatible electrolytic salt. The reservoirs are formed of any material adapted to absorb and hold a sufficient quantity of liquid therein in order to permit the passage of agent therethrough by electrotransport. Preferably, the reservoirs contain one or more hydrophilic polymers such as polyvinylpyrrolidone, polyvinyl alcohol, or polyethylene glycols, and optionally one or more hydrophobic polymers such as polyisobutylene, polyethylene, or polypropylene. The donor electrode 12 and donor reservoir 16 are separated from the counter electrode 14 and the optional counter reservoir 18 by an electrical insulator 20. The insulator 20, may be an air gap or it may be composed of a material which neither conducts electrons nor ions to a substantial extent, and prevents device 10 from short-circuiting through a path which does not include the body surface 100 to which the device 10 is applied. The device 10 optionally includes a backing layer 22 composed of a water-proof and preferably electrically insulating material. Device 10 has an electronic circuit, illustrated schematically in FIG. 1 as a layer 24, and an electric power source, e.g. one or more batteries, therein. Typically, the electronic circuit layer 24 is relatively thin and preferably comprised of electronically conductive pathways printed, painted or otherwise deposited on a thin, flexible substrate such as, for example, a film or polymeric web, e.g. the electronic circuit layer 24, which is a printed flexible circuit. In addition to the power source, the electronic circuit layer 24 may also include one or more electronic components which control the level, waveform shape, polarity, timing, and the like, of the electric current applied by device 10. For example, circuit layer 24 may contain one or more of a control circuitry such as a current controller, e.g. a resistor or a transistor-based current control circuit, an on/off switch, and/or a microprocessor adapted to control the current output of the power source over time. The outputs of circuit layer 24 are electrically connected to electrodes 12 and 14 such that each electrode is in electrical contact with an opposite pole of the power source within circuit layer 24. The device 10 adheres to the body surface 100 in this embodiment by means of a peripheral adhesive layer 28. Optionally, the device may contain an in-line 20 adhesive layer, i.e. an adhesive layer positioned between the donor and/or counter reservoirs 16 and 18 and the patient's body surface. An in-line adhesive must contain an ion-transmitting material, i.e. therapeutic agent ions must be capable of penetrating the adhesive layer to reach the body surface. An optional flux control membrane 30 is positioned between donor reservoir 16 and body surface 100 in order to limit or control the amount of passive, i.e. not electrically assisted, flux of agent to body surface 100 when the device 10 is in an "off" mode.

Base agents which are reacted with an acid enhancer to form an agent-enhancer compound are preferably delivered from the anodic electrode of an electrotransport delivery device while acid agents which are reacted with a base enhancer to form an agent-enhancer compound are preferably delivered from the cathodic electrode of an electrotransport delivery device.

The electrotransport delivery device may be operated in a manner which allows the permeation enhancer ions to be delivered into the patient's body surface at the beginning of agent delivery so that more of the agent is delivered under conditions when the body surface exhibits enhanced flux of agent therethrough. This may be accomplished in several ways. Since the enhancer ions have the opposite charge as the drug ions, the enhancer ions are not delivered by electromigration when the polarity of the donor electrode is such as to deliver the oppositely charged agent ions by electromigration. In order to overcome this problem, the polarity of the electrodes may be switched at the beginning of electrotransport device operation so as to deliver the enhancer ions by electromigration. After a sufficient amount of enhancer is delivered into the animal's body surface in order to achieve a permeation enhancing effect, the polarity of the electrodes can be switched back to the polarity where the agent is delivered to the patient by electromigration. Another way of delivering the enhancer before the agent is to apply the electrotransport donor reservoir to the patient but refrain from turning on the electrotransport current until a sufficient quantity of enhancer is delivered into the body surface by passive diffusion. Once a sufficient (ie, a permeation enhancing) amount of the enhancer has passively diffused into the body surface, the electrotransport device can be activated to apply electrotransport current whereby the agent is delivered by electromigration.

Having thus generally described the invention and certain preferred embodiments thereof, the invention will be further described by reference to the following detailed examples.

EXAMPLES

Example 1

In the following experiments, aqueous solutions of lidocaine hydrolaurate were used as donor solutions to measure in vitro transdermal electrotransport flux of lidocaine. The lidocaine hydrolaurate solutions were formed by reacting (ie, by mixing) lidocaine base and lauric acid.

Figure 2:
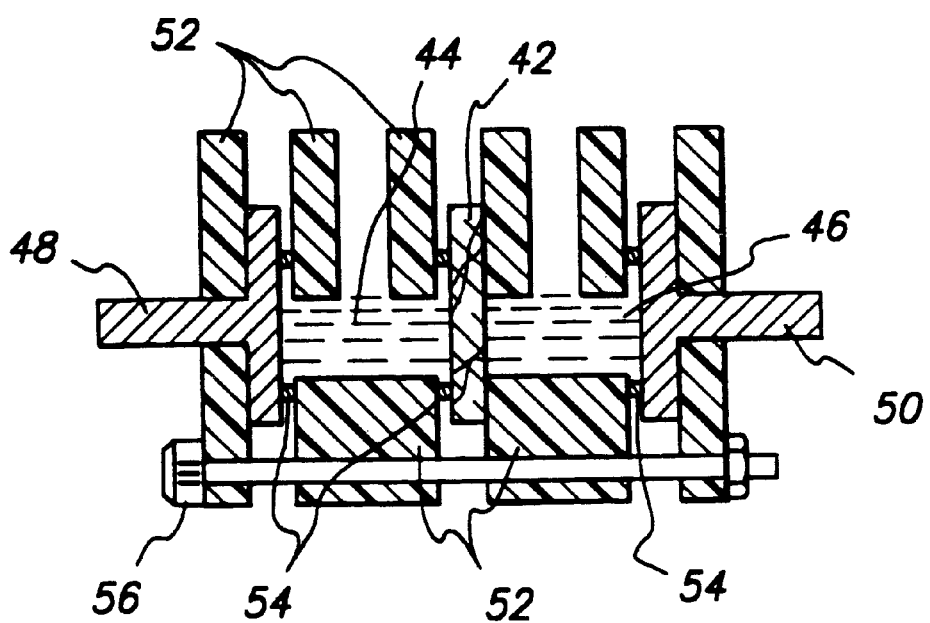
FIG. 2 is a schematic view of an electrotransport system, with parts shown in section, having donor and counter electrodes connected to a remote electrical power source.

Pieces of heat stripped human epidermis obtained from the thigh and breast of human cadavers were mounted in a 2-compartment electrotransport permeation cell illustrated in FIG. 2. Cell 40 was composed predominately of polycarbonate pieces 52 held together with a bolt and nut 56. Cell 40 had a silver foil anodic donor electrode 48 and a Ag/AgCl loaded ethylene vinyl acetate polymer film as the cathodic receptor electrode 50. The donor and receptor electrodes 48,50 were electrically connected to a galvanostat (not shown in FIG. 2) which was set to apply a constant electric current of 126 $\mu$A. The area of each skin sample 42 exposed to electrotransport was about 1.26 cm$^2$ and the volume of each of the donor compartment 44 and the receptor compartment 46 was about 2 mL. The compartments 44 and 46 were sealed using O-rings 54. Solutions containing selected combinations of lidocaine base, lauric acid, and lidocaine HCl were placed in the donor compartment 44. Dulbecco's phosphate buffered saline (an aqueous 0.15 N NaCl solution with minor amounts of other ions, buffered to pH 7.0) was added to the receptor compartment 46. The permeation cell 40 was maintained at about 32° C. throughout each flux experiment. The rate of transdermal electrotransport of the drug was determined by periodically sampling the receptor solution and assaying for lidocaine content. The lidocaine flux was calculated from hourly measurements of the receptor solution over a 6 hour period. The effect of adding a solubilizing agent (ethanol at 25 wt %) to the donor solution was separately tested.

Lidocaine hydrolaurate solutions were prepared having the compositions shown in Table 1. The average lidocaine electrotransport fluxes (ie, average lidocaine transdermal fluxes at times 3 hours through 6 hours of the 6 hour experiment) of various compositions were compared. The overall lidocaine concentration in the donor compartment was held nearly constant in the three formulations by balancing the relative amounts of lidocaine HCl and lidocaine base.

TABLE 1

| Formulation No. | 1 | 2 | 3 |
|---|---|---|---|
| Lidocaine hydrolaurate (mmoles) | 0.50 | 0.75 | 0.50 |
| Lidocaine HCl (mmoles) | 0.50 | 0.25 | 0.50 |
| Ethanol (Weight %) | 0 | 0 | 25% |
| Average Flux (Thigh Skin) ($\mu$g/cm$^2$-hr) | 260 | 300 | 400 |
| Average Flux (Breast Skin) ($\mu$g/cm$^2$-hr) | 130 | 140 | 210 |

As can be seen by comparing the fluxes of formulation Nos. 1 and 2, the lidocaine flux increased by increasing the molar fraction of the lidocaine present as the hydrolaurate salt. As can be seen by comparing the fluxes of formulation Nos. 1 and 3, the addition of 25% ethanol further increases lidocaine flux.

Example 2

Additional Lidocaine Hydrolaurate Formulations

Polyvinyl alcohol (PVOH) hydrogel based donor reservoirs containing aqueous solutions of lidocaine hydrolaurate were prepared with the components mixed in the proportions shown in formulation Nos. 4 and 6 in Table 2. For a comparison with formulation 4, a similar formulation without lauric acid (formulation 5) was also prepared.

TABLE 2

| Formulation No. | 4 (wt %) | 5 (wt %) | 6 (wt %) |
|---|---|---|---|
| PVOH | 13.0 | 13.0 | 11.6 |
| Lidocaine HCL | 4.5 | 4.5 | 2.0 |
| Lidocaine Base | 0.5 | 0.5 | 0.4 |
| Lauric Acid | 0.2 | — | 0.2 |
| Ethanol | 5.0 | 5.0 | 25.1 |
| Water | 76.8 | 77.0 | 60.8 |
| pH | 6.8 | 6.9 | 6.8 |

The components were mixed thoroughly in a beaker placed in a water bath at 50° C. Several gels having a diameter of 1.3 cm (½ inch) and a thickness of 1.6 mm (¹⁄₁₆ inch) were prepared from each formulation in foam molds, and cured at −20° C. overnight, except for gel formulation 6 which was cured overnight at −80° C. The gels were then placed at room temperature. No transdermal flux experiments were conducted using the gels of formulations Nos. 4, 5 and 6.

Example 3

Additional Lidocaine Hydrolaurate Formulations

The formulations shown in Table 3 were prepared by mixing the components at 50° C. and then gels were prepared therefrom and cured overnight at −20° C. The gels were then placed at room temperature.

TABLE 3

| Formulation No. | 7 (wt %) | 8 (wt %) | 9 (wt %) | 10 (wt %) |
|---|---|---|---|---|
| PVOH | 11.6 | 11.6 | 11.6 | 13.0 |
| Lidocaine HCL | 2.0 | 2.0 | 2.0 | 2.5 |
| Lidocaine Base | 0.4 | 0.4 | 0.4 | — |
| Lauric Acid | 0.2 | 0.2 | 0.2 | — |
| Ethanol | 24.9 | 24.8 | 25.0 | — |
| Water | 60.9 | 61.0 | 60.8 | 84.5 |

Gels of formulations 9 and 10 were prepared by mixing the components at 50° C., pipetting the mixture into foam molds and curing overnight at −80° C. The cured gels had a weight of about 0.67 g and a disk shape with a diameter of 2.25 cm and a thickness of 1.6 mm. The gels were used as anodic donor reservoirs of anodic electrode assemblies having a silver foil anode in contact with the body distal surface of the gel and a Medpar backing over the silver foil. The counter electrode assemblies had similar PVOH based gels (but with NaCl in place of the lidocaine salt/base, lauric acid and ethanol) with a cathode comprised of a polymer film loaded with silver chloride powder on the counter gels' body distal surface. The electrode assemblies were applied to separate skin sites on the volunteers and the electrodes were then electrically connected to a Phoresor II power source (sold by Iomed, Inc. Salt Lake City, Utah). The Phoresor II power source was set to apply a current of 1.0 mA (0.25 mA/cm$^2$).

The Phoresor II powered electrode assemblies were applied to 8 healthy human subjects to determine the effectiveness of these formulations in inducing local anesthesia. The lidocaine was administered to the upper arms of the subjects for a 10 minute application period. Five minutes after removal of the systems, testing was initiated to determine the degree and depth of the anesthetic block. The efficacy of the anesthetic block was evaluated by determining the size of the area anesthetized, the depth of the block and the duration of anesthesia. A 27 gauge needle was inserted to a depth of 0.5 mm at the center of the anode skin contact site and sequentially in 1 mm increments away from the center until the perimeter of the site is reached. If the subject reported no pain, the depth of anesthesia was test as follows. The depth of anesthesia was determined by inserting a 20 gauge needle, marked in 1 mm lengths, into the center of the anode skin contact site. The needle was inserted in 1 mm increments, at 5 sec intervals, until the subject reported feeling pain. Once pain was reported, the depth of penetration by the needle was reported. The mean values for the measured parameters are shown in Table 4.

TABLE 4

| Formulation No. | 9 | 10 |
|---|---|---|
| Applied Current (mA) | 1.0 | 0.3 |
| Maximum Time of Surface Anesthesia (min) | 11.0 | 6.0 |
| Maximum Distance from Center (mm) | 10.0 | 8.0 |
| Maximum Depth of Anesthesia (mm) | 8.0 | 5.0 |

As shown in Table 4, the addition of lidocaine hydrolaurate (formulation 9) improves the degree (ie, time, distance from center and depth) of anesthesia compared to lidocaine HCl alone (formulation 10).

Having thus generally described the invention and certain preferred embodiments thereof, it will be readily apparent to a person with skill in the art that various modifications to the invention may be made without departing from the scope of this invention.

We claim:

1. A donor reservoir for an electrotransport therapeutic agent delivery device, the reservoir containing a composition comprising a therapeutic agent-permeation enhancer compound and a liquid solvent for the therapeutic agent-permeation enhancer compound wherein therapeutic agent ions and permeation enhancer ions of opposite charge are formed in the donor reservoir when the therapeutic agent-permeation enhancer compound dissolves in the liquid solvent, the permeation enhancer ions being effective to enhance electrotransport flux of the therapeutic agent ions through a body surface.

2. The reservoir of claim 1, wherein the liquid solvent is an aqueous solvent.

3. The reservoir of claim 1, wherein the therapeutic agent-permeation enhancer compound is a product of a reaction selected from the group consisting of:
a reaction of a base therapeutic agent and an acid permeation enhancer; and
a reaction of an acid therapeutic agent and a base permeation enhancer.

4. The reservoir of claim 1, wherein the therapeutic agent ions comprise a protonated base agent.

5. The reservoir of claim 1, wherein the therapeutic agent ions comprise a deprotonated acid agent.

6. The reservoir of claim 1, wherein the therapeutic agent-permeation enhancer compound comprises a fatty acid drug salt.

7. The reservoir of claim 1, wherein the therapeutic agent comprises at least one amino group.

8. The reservoir of claim 1, wherein the therapeutic agent comprises a drug.

9. The reservoir of claim 1, wherein the therapeutic agent comprises a polypeptide or protein.

10. The reservoir of claim 3, wherein the acid permeation enhancer comprises a $C_8$–$C_{18}$ saturated or unsaturated organic acid.

11. The reservoir of claim 10, wherein the organic acid comprises a $C_{10}$–$C_{14}$ organic acid.

12. The reservoir of claim 10, wherein the organic acid is selected from the group consisting of lauric acid, decanoic acid, myristic acid, and mixtures thereof.

13. The reservoir of claim 1, wherein the composition is substantially free of ions having the same charge as the agent ions.

14. An electrotransport delivery device for delivering a therapeutic agent through a body surface, the device comprising a donor electrode, a counter electrode and an electric power source electrically connected to the donor electrode and the counter electrode, said donor electrode being in electric contact with a donor reservoir containing a composition comprising a therapeutic agent-permeation enhancer compound and a liquid solvent for the therapeutic agent-permeation enhancer compound wherein therapeutic agent ions and permeation enhancer ions of opposite charge are formed in the donor reservoir when the therapeutic agent-permeation enhancer compound dissolves in the liquid solvent, the permeation enhancer ions being effective to enhance electrotransport flux of the therapeutic agent ions through a body surface.

15. The electrotransport delivery device of claim 14, wherein the therapeutic agent-permeation enhancer compound is formed prior to being placed in the donor reservoir.

16. A method of making an electrotransport delivery device for delivering a therapeutic agent through a body surface comprising:
performing a reaction selected from the group consisting of: (i) reacting a base therapeutic agent with an acid permeation enhancer to form a therapeutic agent-permeation enhancer compound and (ii) reacting an acid therapeutic agent with a base permeation enhancer to form a therapeutic agent-permeation enhancer compound wherein the therapeutic agent-permeation enhancer compound when dissolved in a liquid solvent, forms a solution containing therapeutic agent ions and permeation enhancer ions of opposite charge; and
placing the agent-enhancer compound, or a solution thereof, in a donor reservoir of an electrotransport delivery device.

17. The method of claim 16, wherein the therapeutic agent ions comprise a protonated base agent.

18. The method of claim 16, wherein the therapeutic agent ions comprise a deprotonated acid agent.

19. The method of claim 16, wherein the therapeutic agent-permeation enhancer compound comprises a fatty acid drug salt.

20. The method of claim 16, wherein the therapeutic agent comprises at least one amino group.

21. The method of claim 16, wherein the therapeutic agent comprises a drug.

22. The method of claim 16, wherein the therapeutic agent comprises a polypeptide or protein.

23. The method of claim 16, wherein the acid permeation enhancer comprises a $C_8$–$C_{18}$ saturated or unsaturated organic acid.

24. The method of claim 23, wherein the organic acid comprises a $C_{10}$–$C_{14}$ organic acid.

25. The method of claim 23, wherein the organic acid is selected from a group consisting of lauric acid, decanoic acid, myristic acid, and mixtures thereof.

* * * * *